United States Patent [19]

Lee

[11] 4,456,465
[45] Jun. 26, 1984

[54] PHENOXY- AND PYRIDYLOXY-PHENYLPHOSPHINATES AND THEIR USE IN WEED CONTROL

[75] Inventor: Shy-Fuh Lee, Sunnyvale, Calif.

[73] Assignee: Zoecon Corporation, Palo Alto, Calif.

[21] Appl. No.: 456,913

[22] Filed: Jan. 10, 1983

Related U.S. Application Data

[63] Continuation of Ser. No. 309,945, Oct. 9, 1981, abandoned.

[51] Int. Cl.³ .................. C07F 9/32; C07D 213/04; A01N 57/14; A01N 57/16
[52] U.S. Cl. .................................. 71/87; 71/86; 260/940; 260/944; 260/947; 260/951; 546/24; 549/218; 549/220; 564/12

[58] Field of Search .............. 260/940, 951, 944, 947; 71/86, 87; 546/24; 549/218, 220; 564/12

[56] References Cited

U.S. PATENT DOCUMENTS 4,322,375 3/1982 Maier et al. .................. 260/951

Primary Examiner—J. E. Evans
Attorney, Agent, or Firm—Donald W. Erickson; Jacqueline S. Larson

[57] ABSTRACT

Novel phenoxyphenyl-substituted or pyridyloxyphenyl-substituted phosphinates and phosphinothioates, syntheses thereof, intermediates therefor, and the use of said novel phosphinates and phosphinothioates for the control of weeds.

15 Claims, No Drawings

PHENOXY- AND PYRIDYLOXY-PHENYLPHOSPHINATES AND THEIR USE IN WEED CONTROL

This is a continuation of application Ser. No. 309,945, filed Oct. 9, 1981 now abandoned.

The present invention relates to novel phenoxyphenyl-substituted or pyridyloxyphenyl-substituted phosphinates and phosphinothioates, synthesis thereof, intermediates therefor, and the use of said novel phosphinates and phosphinothioates for the control of weeds.

More particularly, the compounds of the present invention are represented by the following formula (A):

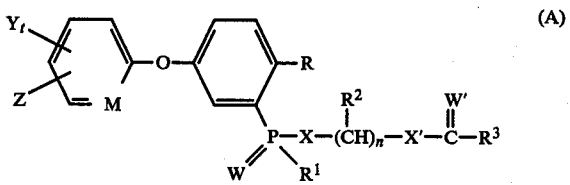

wherein,
n is one, two or three;
t is zero, one or two;
M is CH or N;
R is cyano, nitro, amino or chloro;
$R^1$ is lower alkyl or phenyl;
$R^2$ is hydrogen or lower alkyl, or substituted or unsubstituted phenyl;
$R^3$ is lower alkyl, lower alkenyl, lower haloalkyl, lower cycloalkyl, substituted or unsubstituted phenyl, or lower alkoxy; or $R^2$ and $R^3$ together form an alkylene group of two to four carbon atoms; or $R^2$ and $R^3$ each forms a carbon-carbon bond to adjacent carbon atoms of a benzene ring, provided that n is one, X' is oxygen and W' is oxygen;
each of W and W' is independently selected from oxygen or sulfur;
each of X and X' is independently selected from oxygen, sulfur or amino; and
each of Y and Z is independently selected from hydrogen lower alkyl, lower alkoxy, lower haloalkyl, lower haloalkoxy, halogen, cyano or nitro.

In the description and claims hereinafter, each of M, R–$R^3$, n, t, W, W', X, X', Y, and Z is as defined above, unless otherwise specified.

Compounds of the present invention may be synthesized as outlined below (XX=Cl or Br):

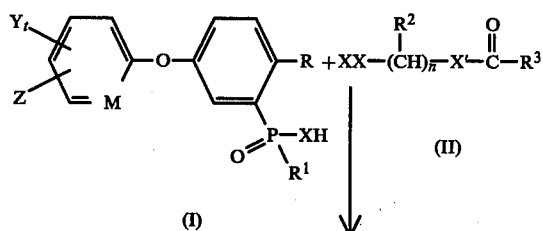

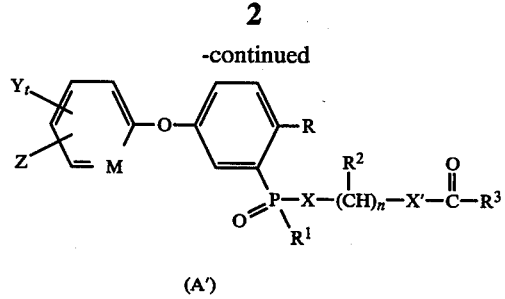

In the above synthesis, a phosphinic acid or phosphinic thioacid (I) is reacted with a haloalkyl carboxylate, thiocarboxylate or amide (II) at room temperature or above in the presence of triethylamine and a solvent such as dimethylformamide or triethylamine to give a phosphinate (A').

Compounds of formula (II) may be prepared by the method described by Ulich and Adams *J.A.C.S.* 43:660 (1921).

Phosphinic acids and thioacids of formula (I) useful as starting acids in the synthesis of compounds of this invention include, but are not restricted to, P-ethyl-2-nitro-5-(4-chlorophenoxy)phenylphosphinic acid, P-ethyl-2-nitro-5-(4-trifluoromethylphenoxy)phenylphosphinic acid, P-ethyl-2-nitro-5-(2,4-dichlorophenoxy)phenylphosphinic acid, P-ethyl-2-nitro-5-(2-chloro-4-trifluoromethylphenoxy)phenylphosphinic acid, P-methyl-2-nitro-5-(2,4-dichlorophenoxy)phenylphosphinic acid, P-methyl-2-nitro-5-(2-chloro-4-trifluoromethylphenoxy)phenyl phosphinic acid, P-ethyl-2-amino-5-(2-chloro-4-trifluoromethyl phenoxy)phenylphosphinic acid, P-ethyl-2-cyano-5-(2-chloro-4-trifluoromethylphenoxy)phenylphosphinic acid, P-ethyl-2-nitro-5-(2,4-dichlorophenoxy)phosphinic thioacid, P-ethyl-2-nitro-5-(2-chloro-4-trifluoromethylphenoxy)phenylphosphinic thioacid, P-ethyl-2-nitro-5-(3,5-dichloro-2-pyridyloxy)phenylphosphinic acid, P-ethyl-2-nitro-5-(3-chloro-5-trifluoromethyl-2-pyridyloxy)phenylphosphinic acid, and P-ethyl-2-nitro-5-(3-chloro-5-trifluoromethyl-2-pyridyloxy)phenylphosphinic thioacid. Examples of the synthesis of such acids and thioacids are presented in U.S. application Ser. No. 276,444, filed June 22, 1981, the entire disclosure of which is incorporated herein by reference.

Compounds of the present invention may also be prepared as outlined below (XX=Cl or Br):

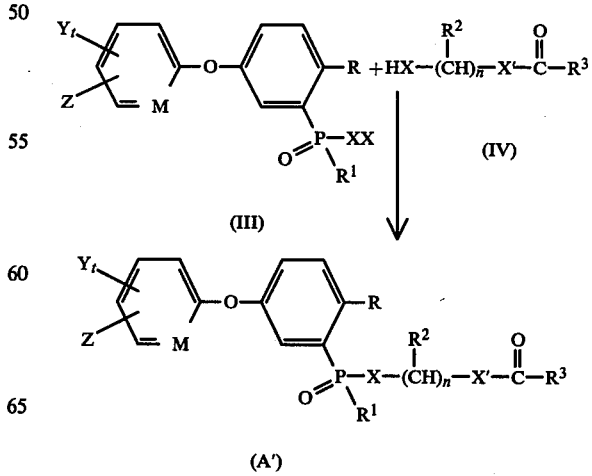

In the above synthesis, a phosphinic halide (III) is reacted with a carboxylate, a thiocarboxylate or an amide corresponding to formula (IV), most usually at room temperature, in the presence of a solvent such as methylene chloride, tetrahydrofuran or dimethylformamide and with or without a base such as triethylamine or pyridine.

Phosphinic halides of formula (III) useful as starting materials in the synthesis of compounds of this invention include, but are not restricted to, P-ethyl-2-nitro-5-(4-chlorophenoxy)phenylphosphinic chloride, P-ethyl-2-nitro-5-(4-trifluoromethylphenoxy)phenylphosphinic chloride, P-ethyl-2-nitro-5-(2,4-dichlorophenoxy)-phenylphosphinic chloride, P-ethyl-2-nitro-5-(2-chloro-4-trifluoromethylphenoxy)phenylphosphinic chloride, P-methyl-2-nitro-5-(2-chloro-4-trifluoromethylphenoxy)phenylphosphinic chloride, P-ethyl-2-cyano-(5-(2-chloro-4-trifluoromethylphenoxy)phenylphosphinic chloride), P-ethyl-2-amino-5-(2-chloro-4-trifluoromethylphenoxy)phenylphosphinic chloride, P-ethyl-2-nitro-5-(3,5-dichloro-2-pyridyloxy)phenylphosphinic chloride and P-ethyl-2-nitro-5-(3-chloro-5-trifluoromethyl-2-pyridyloxy)phenylphosphinic chloride. Examples of the synthesis of such phosphinic halides are presented in copending U.S. application Ser. No. 276,444.

Phosphinothioates of the present invention of formula (A) (where W=sulfur) can be prepared by reaction of a phosphinate (A where W=oxygen) with, for example, phosphorus pentasulfide at an elevated temperature.

Phosphinates of formula (A) where W'=sulfur may be prepared by reacting a phosphinate (A where W'=oxygen) with Lawesson's reagent at an elevated temperature in a solvent such as xylene.

The following terms, wherever used in the description herein and in the appended claims, have the meaning defined below, unless otherwise specified hereinafter.

The term "lower alkyl" refers to an alkyl group, straight or branched, having a chain length of one to eight carbon atoms. The term "lower haloalkyl" refers to a lower alkyl group substituted with one to three halogen atoms.

The term "lower alkoxy" refers to an alkoxy group, straight or branched, having a chain length of one to eight carbon atoms. The term "lower haloalkoxy" refers to a lower alkoxy group substituted with one to three halogen atoms.

The term "lower alkenyl" refers to an ethylenically unsaturated hydrocarbon group, straight or branched, having a chain length of two to eight carbon atoms and one or two ethylenic bonds.

The term "lower cycloalkyl" refers to a cycloalkyl group of three to eight cyclic carbon atoms.

The term "substituted phenyl" refers to a phenyl group substituted at one, two or three of the ring carbon atoms with a group selected from lower alkyl, lower haloalkyl, lower alkoxy, lower alkenyl, lower haloalkenyl, lower alkenyloxy, halogen, nitro, cyano or lower alkylthio.

The novel compounds of formula (A) are useful for the control of weeds, using pre- or post-emergent treatments. The compounds can be applied in the form of dusts, granules, solutions, emulsions, wettable powders, flowables and suspensions. Application of a compound of the present invention is made according to conventional procedure to the weeds or their locus using an herbicidally effective amount of the compounds, usually from about one-half or less to ten pounds per acre.

Methods of preparing herbicidal formulations which can be used with a compound of the present invention are described in the literature along with suitable liquid and solid carriers, such as in U.S. Pat. Nos. 4,192,669 and 4,163,661, which are incorporated herein by reference. The compounds of the present invention have herbicidal activity on both broad leaf plants and the grassy weeds or graminaceous weeds. The optimum usage of a compound of the present invention is readily determinable by one of ordinary skill in the art using routine testing such as greenhouse testing and small plot testing.

The term "herbicide," as used herein, refers to an active ingredient which modifies the growth of plants because of phytotoxic or plant growth regulating properties so as to retard the growth of the plant or damage the plant sufficiently to kill it.

The compounds of the present invention demonstrate selective activity as herbicides against certain weeds. Crops such as rice, corn and soybeans show excellent tolerance. The compounds of the present invention, in general, appear to show a higher level of herbicidal activity when the preemergent method of application is used.

The following examples are provided to illustrate the practice of the present invention. Temperature is given in degrees Centigrade. "RT" means room temperature.

EXAMPLE 1

A mixture of P-ethyl-2-nitro-5-(2-chloro-4-trifluoromethylphenoxy)phenylphosphinic acid (0.33 g, 0.80 mmol), chloromethyl 2,2-dimethylpropanoate (0.24 g, 1.60 mmol), triethylamine (0.22 ml) and dimethylformamide (DMF) (3 ml) is stirred at RT for 2 days. The reaction is then diluted with methylene chloride, washed, dried and evaporated to dryness, followed by purification by preparative thin layer chromatography (prep. TLC) (silica gel, eluting with 40% ethyl acetate/-hexane) to yield 2,2-dimethylpropionyloxymethyl P-ethyl-2-nitro-5-(2-chloro-4-trifluoromethylphenoxy)-phenylphosphinate.

nmr (CDCl₃) δ 1.87–3.10 (m, 6H, aromatic), 4.40 (d, 2H, 12 Hz, —P—O—CH₂—O—), 7.65 (sextet, 2H, —P—CH₂—), 8.90 (s, 9H,

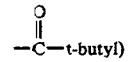

and 8.70–9.07 ppm (tt, 3H, —P—CH₂CH₃).

EXAMPLE 2

A mixture of P-ethyl-2-nitro-5-(2-chloro-4-trifluoromethylphenoxy)phenylphosphinic acid (0.40 g, 0.97 mmol), chloromethyl benzoate (0.23 g, 1.36 mmol) and triethylamine (0.27 g) in 4 ml of DMF is stirred at RT for 4 days. The reaction mixture is poured into water and extracted with methylene chloride. The combined extracts are washed, dried, evaporated to dryness and purified by prep. TLC (eluting with 50% ethyl acetate/hexane) to yield benzoyloxymethyl P-ethyl-2-nitro-5-(2-chloro-4-trifluoromethylphenoxy)phenyl-phosphinate.

nmr (CDCl₃) δ 2.04–3.20 (m, 11H, aromatic), 4.15 (d, 12H, —P—O—CH₂O—), 7.65 (sextet, 2H, —P—CH$_2$—) and 8.67–9.04 ppm (tt, 3H, —P—CH$_2$CH$_3$).

In like manner, 4-chlorobenzoyloxymethyl P-ethyl-2-nitro-5-(2-chloro-4-trifluoromethylphenoxy)phenylphosphinate is prepared from chloromethyl 4-chlorobenzoate and P-ethyl-2-nitro-5-(2-chloro-4-trifluoromethylphenoxy)phenylphosphinic acid.

EXAMPLE 3

Following the procedures of Example 1, P-ethyl-2-nitro-5-(2,4-dichlorophenoxy)phenylphosphinic acid (0.30 g, 0.80 mmol) and chloromethyl 2,2-dimethylpropanoate (0.24 g, 1.6 mmol) are reacted together in the presence of triethylamine (0.23 ml) and DMF (3 ml) to give 2,2-dimethylpropionyloxymethyl P-ethyl-2-nitro-5-(2,4-dichlorophenoxy)phenylphosphinate.

nmr (CDCl$_3$) δ 1.87–3.14 (m, 6H, aromatic), 4.37 (d, 2H, 12 Hz, —P—O—CH$_2$—O—), 7.65 (sextet, 2H, —P—CH$_2$—), 8.88 (s, 9H,

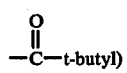
—C—t-butyl)

and 8.67–9.04 ppm (tt, 3H, —P—CH$_2$CH$_3$).

In the same manner, chloromethyl 2,2-dimethylpropanoate is reacted with each of P-ethyl-2-nitro-5-(2-methyl-4-methoxyphenoxy)phenylphosphinic acid, P-ethyl-2-nitro-5-(4-trifluoromethylphenoxy)phenylphosphinic acid, P-ethyl-2-nitro-5-(4-bromo-2-chlorophenoxy)phenylphosphinic acid, P-ethyl-2-nitro-5-(2,4,6-trichlorophenoxy)phenylphosphinic acid and P-ethyl-2-nitro-5-(4-chloro-2-nitrophenoxy)phenylphosphinic acid to yield, respectively, 2,2-dimethylpropionyloxymethyl P-ethyl-2-nitro-5-(2,-methyl-4-methoxyphenoxy)phenylphosphinate,
2,2-dimethylpropionyloxymethyl P-ethyl-2-nitro-5-(4-trifluoromethylphenoxy)phenylphosphinate,
2,2-dimethylpropionyloxymethyl P-ethyl-2-nitro-5-(4-bromo-2-chlorophenoxy)phenylphosphinate,
2,2-dimethylpropionyloxymethyl P-ethyl-2-nitro-5-(2,4,6-trichlorophenoxy)phenylphosphinate, and
2,2-dimethylpropionyloxymethyl P-ethyl-2-nitro-5-(4-chloro-2-nitrophenoxy)phenylphosphinate.

EXAMPLE 4

Following the procedure of Example 1, each of the carboxylates in column I is reacted with P-ethyl-2-nitro-5-(2-chloro-4-trifluoromethylphenoxy)phenylphosphinic acid to yield the phosphinate in column II.

I 1. chloromethyl propanoate
2. chloromethyl acetate
3. chloromethyl chloroacetate
4. chloromethyl 2,2-dichloropropanoate
5. chloromethyl n-butanoate
6. chloromethyl 2-methylpropanoate
7. chloromethyl cyclohexanecarboxylate
8. chloromethyl acrylate
9. α-chloroethyl 2,2-dimethylpropanoate
10. α-chloroethyl benzoate
11. α-chloroethyl acetate
12. α-chloroisobutyl acetate
13. α-chloroisobutyl n-butanoate
14. α-chloroisobutyl 2,2-dimethylpropanoate
15. α-chloroisovaleryl acetate
16. β-chloroethyl 2,2-dimethylpropanoate
17. γ-chloropropyl 2,2-dimethylpropanoate
18. α-chloroethyl 2,2-dichloropropanoate
19. phenylchloromethyl acetate
20. α-chloroethyl ethylcarbonate

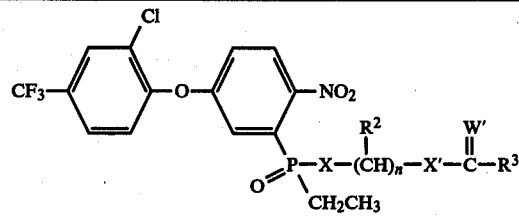

| | X | n | R$_2$ | X' | W' | R$_3$ |
|---|---|---|---|---|---|---|
| 1. | O | 1 | H | O | O | CH$_2$CH$_3$ |
| 2. | O | 1 | H | O | O | CH$_3$ |
| 3. | O | 1 | H | O | O | CH$_2$Cl |
| 4. | O | 1 | H | O | O | C(Cl)$_2$CH$_3$ |
| 5. | O | 1 | H | O | O | CH$_2$CH$_2$CH$_3$ |
| 6. | O | 1 | H | O | O | CH(CH$_3$)$_2$ |
| 7. | O | 1 | H | O | O | C$_6$H$_{11}$ |
| 8. | O | 1 | H | O | O | CH=CH$_2$ |
| 9. | O | 1 | CH$_3$ | O | O | C(CH$_3$)$_3$ |
| 10. | O | 1 | CH$_3$ | O | O | C$_6$H$_5$ |
| 11. | O | 1 | CH$_3$ | O | O | CH$_3$ |
| 12. | O | 1 | CH(CH$_3$)$_2$ | O | O | CH$_3$ |
| 13. | O | 1 | CH(CH$_3$)$_2$ | O | O | CH$_2$CH$_2$CH$_3$ |
| 14. | O | 1 | CH(CH$_3$)$_2$ | O | O | C(CH$_3$)$_3$ |
| 15. | O | 1 | CH$_2$CH(CH$_3$)$_2$ | O | O | CH$_3$ |
| 16. | O | 2 | H | O | O | C(CH$_3$)$_3$ |
| 17. | O | 3 | H | O | O | C(CH$_3$)$_3$ |
| 18. | O | 1 | CH$_3$ | O | O | C(Cl)$_2$CH$_3$ |
| 19. | O | 1 | C$_6$H$_5$ | O | O | CH$_3$ |
| 20. | O | 1 | CH$_3$ | O | O | OCH$_2$CH$_3$ |

The compounds herein, such as those under column II, may be named as derivatives of phosphinate and may also be named as carboxylates. For example, compound 9 above may be named α-(2,2-dimethylpropionyloxy)ethyl P-ethyl-2-nitro-5-(2-chloro-4-trifluoromethylphenoxy)phenylphosphinate as well as α-[P-ethyl-2-nitro-5-(2-chloro-4-trifluoromethylphenoxy)phenylphosphinyloxy]ethyl 2,2-dimethylpropanoate.

EXAMPLE 5

To 2,2-dimethylpropionyloxymethyl P-ethyl-2-nitro-5-(2-chloro-4-trifluoromethylphenoxy)phenylphosphinate (1.0 mmol) in xylene (0.5 ml) is added Lawesson's reagent [2,4-bis(4-methoxyphenyl)-1,3-dithia-2,4-diphosphetane-2,4-disulfide] (2.0 mmol). The mixture is heated at 140° for 24 hours. The solvent is then removed and the crude product is purified by prep. TLC (40% ethyl acetate/hexane) to give 2,2-dimethyl(thiopropionyl)oxymethyl P-ethyl-2-nitro-5-(2-chloro-4-trifluoromethylphenoxyphenylphosphinate.

In the same way, α-methyl[2,2-dimethyl(thiopropionyl)oxy]methyl P-ethyl-2-nitro-5-(2-chloro-4-trifluoromethylphenoxy)phenylphosphinate is prepared from α-methyl(2,2-dimethylpropionyloxy)methyl P-ethyl-2-nitro-5-(2-chloro-4-trifluoromethylphenoxy)-phenylphosphinate and Lawesson's reagent.

EXAMPLE 6

A mixture of 2,2-dimethylpropionyloxymethyl P-ethyl-2-nitro-5-(2-chloro-4-trifluoromethylphenoxy)-phenylphosphinate (4.7 mmol) and phosphorus pentasulfide (1.2 mmol) is heated to 150°–160° under nitrogen for 3–4 hours. After cooling, the residue is purified by prep. TLC (20% ethyl acetate/hexane) to give O-(2,2- dimethylpropionyloxymethyl) P-ethyl-2-nitro-5-(2-chloro-4-trifluoromethylphenoxy)phenylphosphinothioate.

In the same way, 2,2-dimethyl(thiopropionyl)oxymethyl P-ethyl-2-nitro-5-(2-chloro-4-trifluoromethylphenoxy)phenylphosphinate is reacted with phosphorus pentasulfide to yield O-[2,2-dimethyl(thiopropionyl)oxymethyl] P-ethyl-2-nitro-5-(2-chloro-4-trifluoromethylphenoxy)phenylphosphinothioate.

EXAMPLE 7

Following the procedure of Example 1, P-ethyl-2-nitro-5-(2-chloro-4-trifluoromethylphenoxy)phenylphosphinothioic acid is reacted with each of chloromethyl 2,2-dimethylpropanoate, chloromethyl benzoate and 1-chloroethyl propanoate to give, respectively, S-(2,2-dimethylpropionyloxymethyl) P-ethyl-2-nitro-5-(2-chloro-4-trifluoromethylphenoxy)phenylphosphinothioate, S-benzoyloxymethyl P-ethyl-2-nitro-5-(2-chloro-4-trifluoromethylphenoxy)phenylphosphinothioate, and S-[α-methyl(2,2-dimethylpropionyloxy)methyl] P-ethyl-2-nitro-5-(2-chloro-4-trifluoromethylphenoxy)phenylphosphinothioate.

EXAMPLE 8

To a solution of P-ethyl-2-nitro-5-(2-chloro-4-trifluoromethylphenoxy)phenylphosphinic chloride (1.0 mmol) in methylene chloride (5 ml) is added, at 0°, a solution of N-hydroxymethyl-2,2-dimethylpropionamide (1.5 mmol) and triethylamine (1.0 mmol) in methylene chloride (5 ml). This mixture is stirred at RT for 2 hours. The reaction mixture is then diluted with methylene chloride, washed, dried and evaporated to dryness to give, after purification by prep. TLC (60% ethyl acetate/hexane), N-(2,2-dimethylpropionyl)aminomethyl P-ethyl-2-nitro-5-(2-chloro-4-trifluoromethylphenoxy)phenylphosphinate.

In the same way, P-ethyl-2-nitro-5-(2-chloro-4-trifluoromethylphenoxy)phenylphosphinic chloride is reacted with each of N-hydroxymethylacetamide and N-(1-hydroxyethyl)propionamide to yield, respectively, N-acetylaminomethyl P-ethyl-2-nitro-5-(2-chloro-4-trifluoromethylphenoxy)phenylphosphinate and N-[α-methyl(propionylamino)methyl] P-ethyl-2-nitro-5-(2-chloro-4-trifluoromethylphenoxy)phenylphosphinate.

EXAMPLE 9

Following the procedure of Example 1, chloromethyl 2,2-dimethylpropanoate is reacted with each of P-ethyl-2-amino-5-(2-chloro-4-trifluoromethylphenoxy)phenylphosphinic acid, P-ethyl-2-cyano-5-(2-chloro-4-trifluoromethylphenoxy)phenylphosphinic acid and P-ethyl-2-chloro-5-(2-chloro-4-trifluoromethylphenoxy)phenylphosphinic acid to yield respectively, 2,2-dimethylpropionyloxymethyl P-ethyl-2-amino-5-(2-chloro-4-trifluoromethylphenoxy)phenylphosphinate, 2,2-dimethylpropionyloxymethyl P-ethyl-2-cyano-5-(2-chloro-4-trifluoromethylphenoxy)phenylphosphinate, and 2,2-dimethylpropionyloxymethyl P-ethyl-2-chloro-5-(2-chloro-4-trifluoromethylphenoxy)phenylphosphinate.

EXAMPLE 10

Following the procedure of Example 1, chloromethyl 2,2-dimethylpropanoate is reacted with each of P-methyl-2-nitro-5-(2-chloro-4-trifluoromethylphenoxy)phenylphosphinic acid, P-(n-propyl)-2-nitro-5-(2-chloro-4-trifluoromethylphenoxy)phenylphosphinic acid and P-phenyl-2-nitro-5-(2-chloro-4-trifluoromethylphenoxy)phenylphosphinic acid to give, respectively, 2,2-dimethylpropionyloxymethyl P-methyl-2-nitro-5-(2-chloro-4-trifluoromethylphenoxy)phenylphosphinate, 2,2-dimethylpropionyloxymethyl P-(n-propyl)-2-nitro-5-(2-chloro-4-trifluoromethylphenoxy)phenylphosphinate, and 2,2-dimethylpropionyloxymethyl P-phenyl-2-nitro-5-(2-chloro-4-trifluoromethylphenoxy)phenylphosphinate.

EXAMPLE 11

Following the procedure of Example 1, P-ethyl-2-nitro-5-(3-chloro-5-trifluoromethyl-2-pyridyloxy)phenylphosphinic acid is reacted with each of the carboxylates in column III to give the corresponding phosphinate in column IV.

III chloromethyl 2,2-dimethylpropanoate
chloromethyl 4-chlorobenzoate
chloromethyl propanoate
chloromethyl 2,2-dichloropropanoate
chloromethyl chloroacetate
chloromethyl n-butanoate
chloromethyl cyclohexanecarboxylate
α-chloroethyl acetate
α-chloro-β-methylpropyl propanoate
β-chloroethyl 2,2-dimethylpropanoate
α-chloroethyl 2,2-dichloropropanoate
2,2-dimethylpropionyloxymethyl P-ethyl-2-nitro-5-(3-chloro-5-trifluoromethyl-2-pyridyloxy)phenylphosphinate
4-chlorobenzoyloxymethyl P-ethyl-2-nitro-5-(3-chloro-5-trifluoromethyl-2-pyridyloxy)phenylphosphinate
propionyloxymethyl P-ethyl-2-nitro-5-(3-chloro-5-trifluoromethyl-2-pyridyloxy)phenylphosphinate
2,2-dichloropropionyloxymethyl P-ethyl-2-nitro-5-(3-chloro-5-trifluoromethyl-2-pyridyloxy)phenylphosphinate
chloroacetoxymethyl P-ethyl-2-nitro-5-(3-chloro-5-trifluoromethyl-2-pyridyloxy)phenylphosphinate
n-butyryloxymethyl P-ethyl-2-nitro-5-(3-chloro-5-trifluoromethyl-2-pyridyloxy)phenylphosphinate
cyclohexanecarboxymethyl P-ethyl-2-nitro-5-(3-chloro-5-trifluoromethyl-2-pyridyloxy)phenylphosphinate
α-methyl(acetoxy)methyl P-ethyl-2-nitro-5-(3-chloro-5-trifluoromethyl-2-pyridyloxy)phenylphosphinate
α-isopropyl(propionyloxy)methyl P-ethyl-2-nitro-5-(3-chloro-5-trifluoromethyl-2-pyridyloxy)phenylphosphinate
2,2-dimethylpropionyloxyethyl P-ethyl-2-nitro-5-(3-chloro-5-trifluoromethyl-2-pyridyloxy)phenylphosphinate
α-methyl(2,2-dichloropropionyl)methyl P-ethyl-2-nitro-5-(3-chloro-5-trifluoromethyl-2-pyridyloxy)phenylphosphinate

EXAMPLE 12

Following the procedure of Example 1, P-ethyl-2-nitro-5-(2-chloro-4-trifluoromethylphenoxy)phenylphosphinic acid is reacted with each of S-(chloromethyl) 2,2-dimethylpropanothioate and S-(1-chloroethyl) chloroacetothioate to yield, respectively, 2,2-dimethylpropionylthiomethyl P-ethyl-2-nitro-5-(2-chloro-4-trifluoromethylphenoxy)phenylphosphinate and α-methyl-(chloroacetylthio)methyl P-ethyl-2-nitro-5-(2-chloro-4-trifluoromethylphenoxy)phenylphosphinate.

In the same way, P-ethyl-2-nitro-5-(3-chloro-5-trifluoromethyl-2-pyridyloxy)phenylphosphinic acid is reacted with S-(chloromethyl) 2,2-dimethylpropanothioate to give 2,2-dimethylpropionylthiomethyl P-ethyl-2-nitro-5-(3-chloro-5-trifluoromethyl-2-pyridyloxy)-phenylphosphinate.

EXAMPLE 13

Following the procedure of Example 1, P-ethyl-2-nitro-5-(2-chloro-4-trifluoromethylphenoxy)phenylphosphinic acid is reacted with 4-bromo-γ-butyrolactone to give 4-[P-ethyl-2-nitro-5-(2-chloro-4-trifluoromethylphenoxy)phenylphosphinyloxy]-γ-butyrolactone.

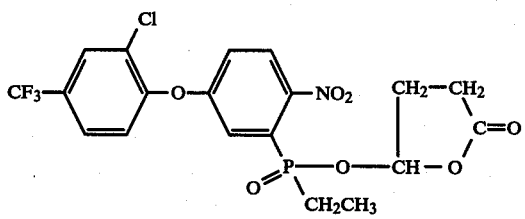

In the same way, P-ethyl-2-nitro-5-(2-chloro-4-trifluoromethylphenoxy)phenylphosphinic acid is reacted with 3-bromophthalide to give 3-[P-ethyl-2-nitro-5-(2-chloro-4-trifluoromethylphenoxy)phenylphosphinyloxy]phthalide (A; Z=CF$_3$, Y=Cl, t=one, M=CH, W=X=X'=W'=O, R=nitro, R$^1$=ethyl, n=1, R$^2$ and R$^3$ each forms a carbon-carbon bond to adjacent carbon atoms of a benzene ring).

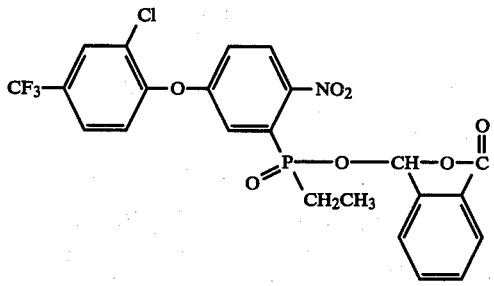

EXAMPLE 14

Post-emergence herbicidal activity on the grasses green foxtail, watergrass, shattercane and wild oats and on the broadleafs annual morning glory, mustard, soybean and velvetleaf was tested for the compound of Example 1 by spraying seedlings with a solution of water/acetone (1:1), surfactant (1%) and the test compound at a rate equivalent to 10 lb./acre. Scoring was made two weeks after spraying. The average herbicidal activity in grasses was 73% and in broadleafs, 100%.

Pre-emergent herbicidal activity of the compound of Example 1 was tested on the above listed grasses and broadleafs (but with nightshade substituted for soybean) at a rate equivalent to 10 lb./acre. Observation showed 100% herbicidal activity in both grasses and broadleafs.

What is claimed is:

1. A compound of the formula (A):

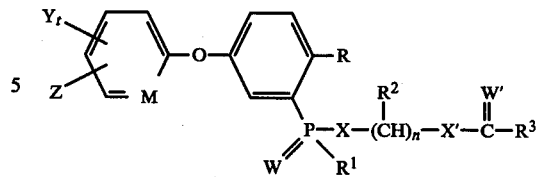

wherein,
n is one, two or three;
t is zero, one or two;
M is CH or N;
R is cyano, nitro, amino or chloro;
R$^1$ is lower alkyl or phenyl;
R$^2$ is hydrogen, lower alkyl or substituted or unsubstituted phenyl;
R$^3$ is lower alkyl, lower alkenyl, lower haloalkyl, lower cycloalkyl, substituted or unsubstituted phenyl, or lower alkoxy; or R$^2$ and R$^3$ together form an alkylene group of two to four carbon atoms; or R$^2$ and R$^3$ each forms a carbon-carbon bond to adjacent carbon atoms of a benzene ring, provided that n is one, X' is oxygen and W' is oxygen;
each of W and W' is independently selected from oxygen or sulfur;
each of X and X' is independently selected from oxygen, sulfur or amino; and
each of Y and Z is independently selected from hydrogen, lower alkyl, lower alkoxy, lower haloalkyl, halogen, cyano or nitro.

2. A compound according to claim 1 wherein M is CH, n is one, R is cyano or nitro, and R$^1$ is methyl or ethyl.

3. A compound according to claim 2 wherein R$^2$ is hydrogen, methyl, ethyl or isopropyl; R$^3$ is methyl, ethyl, propyl, t-butyl, chloromethyl, dichloroethyl, phenyl or 4-chlorophenyl; and W is oxygen.

4. A compound according to claim 3 wherein t is zero or one; Y is hydrogen, chloro or trifluoromethyl; and Z is chloro or trifluoromethyl.

5. A compound according to claim 4 wherein each of X, X' and W' is oxygen.

6. A compound according to claim 5 wherein R$^2$ is hydrogen.

7. A compound according to claim 6 wherein R$^3$ is t-butyl.

8. The compound 2,2-dimethylpropionyloxymethyl P-ethyl-2-nitro-5-(2-chloro-4-trifluoromethylphenoxy)-phenylphosphinate, according to claim 7.

9. A compound according to claim 2 wherein R$^2$ is hydrogen, methyl, ethyl or isopropyl; R$^3$ is methyl, ethyl, propyl, t-butyl, chloromethyl, dichloroethyl, phenyl or 4-chlorophenyl; and W is sulfur.

10. A compound according to claim 1 wherein M is N, n is one, R is cyano or nitro and R$^1$ is methyl or ethyl.

11. A compound according to claim 10 wherein R$^2$ is hydrogen, methyl, ethyl or isopropyl; R$^3$ is methyl, ethyl, propyl, t-butyl, chloromethyl, dichloroethyl, phenyl or 4-chlorophenyl; and W is oxygen.

12. A method for the control of weeds which comprises treating said weed or its locus with a herbicidally effective amount of a compound of formula (A) as defined in claim 1.

13. A composition for the control of weeds which comprises a herbicidally effective amount of a compound of formula (A) as defined in claim 1 and a suitable liquid or solid carrier.

14. A compound according to claim 11 wherein t is one, Y is chloro and Z is trifluoromethyl.

15. A compound according to claim 14 wherein each of X, X' and W' is oxygen.

* * * * *